(12) United States Patent
Jeong et al.

(10) Patent No.: US 12,414,692 B2
(45) Date of Patent: *Sep. 16, 2025

(54) BIO-SIGNAL MEASURING DEVICE AND BIO-SIGNAL MEASURING METHOD

(71) Applicant: ATSENS CO., LTD., Gyeonggi-do (KR)

(72) Inventors: Jong Ook Jeong, Gyeonggi-do (KR); Chang Ho Lee, Gyeonggi-do (KR); Bang Won Lee, Gyeonggi-do (KR)

(73) Assignee: ATSENS CO., LTD., Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/734,183

(22) Filed: Jun. 5, 2024

(65) Prior Publication Data

US 2024/0315558 A1 Sep. 26, 2024

Related U.S. Application Data

(63) Continuation of application No. 17/036,082, filed on Sep. 29, 2020, now Pat. No. 12,029,524.

(51) Int. Cl.
*A61B 5/00* (2006.01)
*G16H 40/63* (2018.01)
*H04L 67/12* (2022.01)

(52) U.S. Cl.
CPC .......... *A61B 5/0002* (2013.01); *A61B 5/6898* (2013.01); *G16H 40/63* (2018.01); *H04L 67/12* (2013.01)

(58) Field of Classification Search
None
See application file for complete search history.

(56) References Cited

U.S. PATENT DOCUMENTS 7,294,105 B1   11/2007  Islam
8,116,888 B2 *  2/2012  Tsai .................... G05B 19/0426
                                                      700/87

(Continued)

FOREIGN PATENT DOCUMENTS

JP    2017079807 A   5/2017
WO    2009112976 A1  9/2009

OTHER PUBLICATIONS

"2nd Office Action", JP_2020159710; Solid composition evaluation apparatus and method for evaluating solid composition using the same, Mar. 14, 2023, 9 pgs.

*Primary Examiner* — Carl H Layno
*Assistant Examiner* — Manolis Pahakis
(74) *Attorney, Agent, or Firm* — Bridgeway IP Law Group, PLLC; Sang Ho Lee; Hyun Woo Shin (57) ABSTRACT

A bio-signal measuring device includes a signal detector detecting a bio-signal, a signal converter converting the bio-signal into a bio-digital signal, a memory, a communicator communicating with an external device, and a processor configured to operate in a first operation mode for storing the bio-digital signal in the memory or a second operation mode for transmitting the bio-digital signal to the external device. An electrocardiogram measuring system and method including a portable electronic device configured to facilitate transmitting an electrocardiogram digital signal from an electrocardiogram measuring device to an external device by pre-storing an identification of the external device, accessing a certificate stored in the external device, and authenticating the certificate of the external device, are also disclosed.

14 Claims, 7 Drawing Sheets

(56) References Cited

U.S. PATENT DOCUMENTS

| | | | |
|---|---|---|---|
| 9,386,401 | B2 | 7/2016 | Gold |
| 9,729,330 | B2 * | 8/2017 | Verma ................... H04L 67/06 |
| 9,774,589 | B2 | 9/2017 | Borchardt et al. |
| 10,798,547 | B2 * | 10/2020 | Gold ..................... G06Q 30/02 |
| 2007/0135855 | A1 | 6/2007 | Foshee et al. |
| 2008/0046037 | A1 | 2/2008 | Haubrich et al. |
| 2009/0231124 | A1 | 9/2009 | Klabunde et al. |
| 2010/0299517 | A1 | 11/2010 | Jukic et al. |
| 2010/0315225 | A1 | 12/2010 | Teague |
| 2011/0004073 | A1 | 1/2011 | Corroy et al. |
| 2011/0145894 | A1 * | 6/2011 | Garcia Morchon .. H04L 63/062 726/4 |
| 2011/0152632 | A1 | 6/2011 | Le et al. |
| 2011/0221590 | A1 | 9/2011 | Baker et al. |
| 2012/0022885 | A1 | 1/2012 | Murayama et al. |
| 2013/0317852 | A1 | 11/2013 | Worrell et al. |
| 2014/0195602 | A1 | 7/2014 | Carricarte et al. |
| 2016/0063189 | A1 | 3/2016 | Soon-Shiong et al. |
| 2016/0337863 | A1 * | 11/2016 | Robinson .............. H04W 4/021 |
| 2017/0372055 | A1 * | 12/2017 | Robinson ............ H04W 12/104 |
| 2019/0189254 | A1 * | 6/2019 | Roennow ............. H04L 9/0637 |
| 2019/0208414 | A1 * | 7/2019 | Roennow ............ G06F 16/1824 |
| 2019/0286806 | A1 * | 9/2019 | Robinson .............. H04W 12/10 |
| 2021/0068762 | A1 | 3/2021 | Park et al. |
| 2021/0118579 | A1 * | 4/2021 | Morris .................. G16H 20/10 |
| 2023/0088697 | A1 * | 3/2023 | Limonta .............. H04L 67/567 713/187 |

* cited by examiner

BIO-SIGNAL MEASURING DEVICE AND BIO-SIGNAL MEASURING METHOD

CROSS-REFERENCE TO RELATED APPLICATION(S)

This application is a continuation of U.S. patent application Ser. No. 17/036,082 filed Sep. 29, 2020, which issued as U.S. Pat. No. 12,029,524, by Jeong et al., entitled "BIO-SIGNAL MEASURING DEVICE AND BIO-SIGNAL MEASURING METHOD." All sections of the aforementioned application(s) are incorporated herein by reference in its entirety.

FIELD OF THE DISCLOSURE

One or more embodiments relate to a bio-signal measuring device and a bio-signal measuring method.

BACKGROUND

In order to maintain human life, there is a need for a process of enabling blood released by the heartbeat to flow along the arteries to all parts of the body without clogging and returning blood through the veins back to the heart. Accordingly, oxygen and nutrients may be supplied to the body's tissues, and consumed wastes may be removed through the metabolism.

However, when the human heart is in a poor condition, blood may not be properly delivered to particular parts of the body or a blood clot or embolism may occur in the blood. As a result, blood may become cloudy, and the cloudy blood may block capillaries, in particular tissues of the body, and cause tissue necrosis, and thus, the human life may be in danger. Therefore, in addition to clinical examinations, imaging tests and the like have been used to examine whether or not the heart is abnormal. Also, as an early diagnosis method, a method of determining whether or not a patient has an abnormality in the heart by measuring an electrocardiogram and displaying the measured electrocardiogram signal on a graph has also been widely used.

In other words, an electrocardiogram refers to recording of a potential change in the surface of the body that causes the mechanical activity of the heartbeat, such as contraction or expansion of the heart muscle. The electrocardiogram is a noninvasive test that is simple to measure, is easily reproduced, is easily repetitively recorded, and is inexpensive to test. The electrocardiogram has been used helpfully to diagnose arrhythmia and coronary artery disease (cardiac artery disease) and to monitor the progress of cardiac patients.

In general, the electrocardiogram is measured by attaching sensors for measuring electrocardiogram signals on the upper left and right and lower left and right of the chest and by using potential differences according to the location of the sensor.

SUMMARY

One or more embodiments include a portable electronic device for receiving bio-signal data from a measuring device and for storing and carrying the bio-signal data.

One or more embodiments include providing, through an output unit of an electronic device connected and communicating with a portable electronic device, bio-signal data stored in the portable electronic device or bio-signal data received through the portable electronic device.

Additional aspects will be set forth in part in the description which follows and, in part, will be apparent from the description, or may be learned by practice of the presented embodiments of the disclosure.

A computer program according to one or more embodiments may be stored on a medium to execute, by using a computer, any one of methods according to one or more methods.

In addition, provided are other methods, other systems, and computer-readable recording media recording thereon a computer program for executing the method.

Other aspects, features, and advantages than those described above will become apparent from the following drawings, claims, and detailed description.

BRIEF DESCRIPTION OF THE DRAWINGS

Reference will now be made to the accompanying drawings, which are not necessarily drawn to scale, and wherein.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

While example embodiments are capable of various modifications and alternative forms, embodiments thereof are shown by way of example in the drawings and will herein be described in detail. The effects and features of the present disclosure and the accompanying methods thereof will become apparent from the following description of the embodiments, taken in conjunction with the accompanying drawings. However, the present disclosure is not limited to the embodiments described below, and may be embodied in various modes.

Hereinafter, one or more embodiments will be described in detail with reference to the accompanying drawings.

Figure 1:
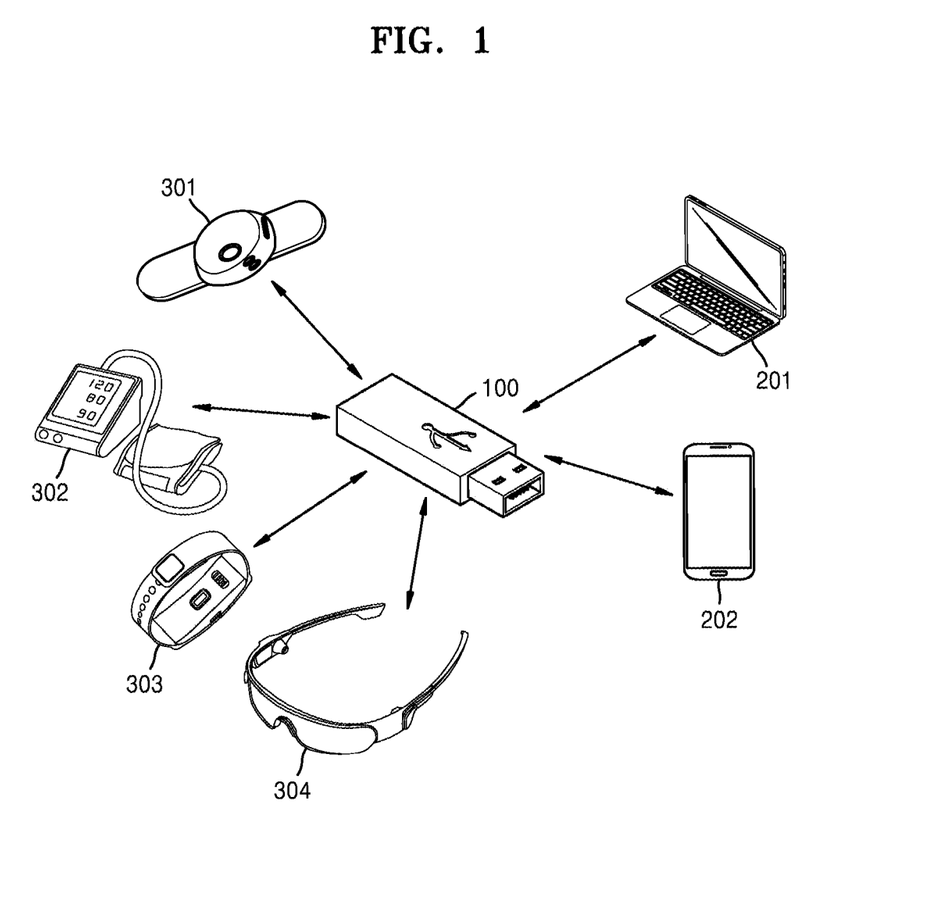
FIG. 1 is a view for explaining a bio-signal data processing system according to one or more embodiments.

FIG. 1 is a view for explaining a bio-signal data processing system according to one or more embodiments.

As shown in FIG. 1, in the bio-signal data processing system, bio-signal measuring devices 301, 302, 303, and 304 (hereinafter referred to as a bio-signal measuring device 300) store bio-signal data by measuring bio-signal data and transmitting the bio-signal data to a portable electronic device 100.

The bio-signal measuring device 300 may be a device for measuring a bio-signal through the body of a user and measure blood pressure, blood sugar, heartrate, oxygen saturation level, sleep time, depression diagnosis, chemical analysis, weight, exercise load, an electrocardiogram, and the like.

The portable electronic device 100 stores, in a memory, the bio-signal data received from the bio-signal measuring device 300. The portable electronic device 100 is connected to a communication port of electronic devices 201 and 202 (hereinafter referred to as an electronic device 200) to perform various operations through the electronic device 200. For example, the portable electronic device 100 may enable the bio-signal data to be output through the electronic device 200. The portable electronic device 100 may transmit the bio-signal data to a preset electronic mail through the electronic device 200. The portable electronic device 100 controls processing, such as preset output, data copy, and data movement, to be performed rather than stores the bio-signal data in the electronic device 200.

The electronic device 200 may include one or more processors and a communication interface for communicating with external devices and may include an output unit with a user interface. As shown in FIG. 1, the electronic device 200 may be a desktop computer 201 or a smartphone 202 but is not limited thereto. The electronic device 200 may be implemented as a smartphone, a table personal computer (PC), a mobile phone, a video phone, an e-book reader, a desktop PC, a laptop PC, a netbook computer, a workstation, a server, a personal digital assistant (PDA), a portable multimedia player (PMP), an MP3 player, a mobile medical device, a camera, a wearable device, or the like.

In the bio-signal data processing system, the bio-signal measuring device 300 refers to a device for measuring bio-signal data. For example, the bio-signal measuring device 300 may be a device which is mounted on an object noninvasively or invasively to detect an electrocardiogram. Here, the object may be a human, an animal, or part of the body of a human or animal such as the chest but is not limited thereto. The object may include all types of objects from which electrocardiograms may be detected or measured. Also, an electrocardiogram is a graph that records changes in a potential on the surface of the body causing the mechanical activity of the heartbeat such as contraction/expansion of the myocardium. Here, the meaning "detect an electrocardiogram" may mean the same as "detect a potential" on the surface of the body.

As shown in FIG. 1, the bio-signal measuring device 300 may be implemented in the form of a wristwatch, glasses, and the like to measure a bio-signal.

The bio-signal measuring device 300 may communicate with the portable electronic device 100 by including a near field communication module. Here, the near field communication module refers to a module for performing communication with an external device located at a short distance, according to near field communication methods such as Bluetooth, radio frequency identification (RFID), infrared data association (IrDA), ultra-wideband (UWB), and Zig-Bee. The bio-signal measuring device 300 may further include a band-type mounting part. The mounting part may be made of a flexible material that may be deformed to fit a curved surface of the surface of the body, for example, an elastic(i.e., flexible) fabric. The mounting part may be provided as a patch-type or a wearable type. As long as the bio-signal measuring device 300 is worn through the mounting part, the bio-signal measuring device 300 may detect a potential generated on the surface of the body by contacting the surface of the body of the object obj.

Figure 2:
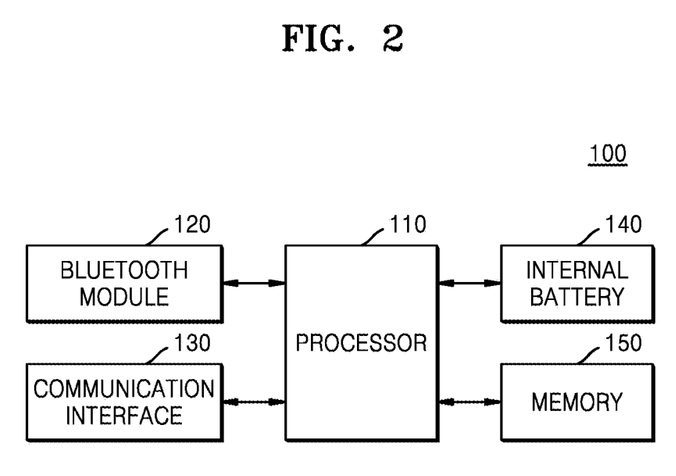
FIG. 2 is a block diagram of a portable electronic device according to one or more embodiments.
Figure 3:
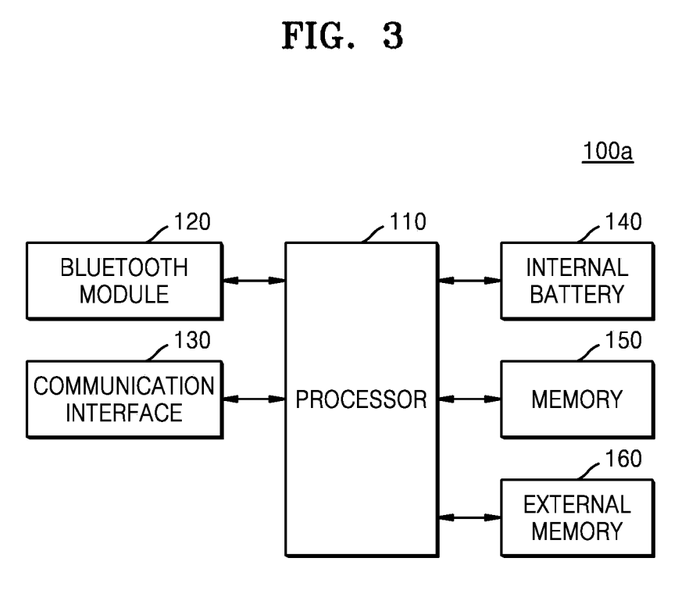
FIG. 3 is a block diagram of a portable electronic device having an external memory according to one or more embodiments.

FIGS. 2 and 3 are block diagrams of portable electronic devices 100 and 100a according to one or more embodiments.

As shown in FIG. 2, the portable electronic device 100 may include a processor 110, a Bluetooth module 120, a communication interface 130, an internal battery 140, and a memory 150.

The processor 110 stores, in the memory 150, bio-signal data received from the bio-signal measuring device 300.

The processor 110 detects communication connection to the electronic device 200 through the communication interface 130. The processor 110 may determine whether or not connection to the electronic device 200 is maintained by authenticating a certificate of the electronic device 200 or a password input from the electronic device 200. For example, the processor 110 accesses the certificate stored in the electronic device 200 to determine whether or not a certificate is approved and maintains connection to the electronic device 200 storing the approved certificate. The processor 110 may determine whether or not the electronic device 200 is approved by transmitting, to the electronic device 200, a control signal for providing a password input screen and receiving a password input through the password input screen.

The processor 110 may transmit, to the electronic device 200 that is connected, bio-signal data or an output control signal of the bio-signal data. For example, the output control signal controls received bio-signal data to be outputted. The output control signal may be changed according to a specification of an output unit of the connected electronic device 200 and may include programming to be dynamically changed according to a user input value from the electronic device 200.

The processor 110 may transmit a stored signal of the bio-signal data to the connected electronic device 200. The electronic device 200 stores the bio-signal data in the memory 150 in response to the stored signal.

The processor 110 may identify the electronic device 200 on the basis of an ID of the electronic device 200 and transmit a control signal to transmit the bio-signal data to a mail address corresponding to the electronic device 200. The processor 110 may identify the validity of the ID of the electronic device 200 through an external server. The processor 110 may pre-store the ID of the electronic device 200 associated with the portable electronic device 100 and refer to the pre-stored ID of the electronic device 200.

The electronic device 200 received the bio-signal data to a preset mail address in response to the control signal from the processor 110. In another embodiment, the processor 110 may search for the ID of the electronic device 200 and store the bio-signal data in a storage area corresponding to the ID of the electronic device 200.

The Bluetooth module 120 receives the measured bio-signal data by communicating with the bio-signal measuring device 300. The Bluetooth module 120 may be designed to communicate with the bio-signal measuring device 300 according to a time point at which the bio-signal measuring device 300 measures a bio-signal. The processor 110 stores, in the memory 150, the bio-signal data received through the Bluetooth module 120. The portable electronic device 100 may further include a state for notifying an operation of the Bluetooth module 120 or the like. The Bluetooth module 120 may receive and transmit data by using a frequency band of about 2400 MHZ to about 2483.5 MHZ. The Bluetooth module 120 may receive and transmit data while hopping one or more frequencies from among frequencies within a frequency band. For example, the Bluetooth module 120 may operate by receiving first data at a first frequency in one communication session and then changing the first frequency to a second frequency to receive second data.

The communication interface 130 may transmit the bio-signal data and the control signal to the electronic device 200. The processor 110 stores, in the memory 150, data received through the Bluetooth module 120 and transmits in real time, to the electronic device 200, data received through the communication interface 130. FIG. 1 illustrates that the communication interface 130 is a wired USB, but the communication interface 130 may be a wireless method.

The internal battery 140 supplies power to each component of the portable electronic device 100. The internal battery 140 may supply power so that data is transmitted and received through the Bluetooth module 120 and/or the communication interface 130. The internal battery 140 may be a lithium iron phosphate (LiFePO4) battery but is not limited thereto and may be manufactured as a lithium cobalt oxide (LiCoO2) battery, a lithium titanate battery, or the like. The internal battery 140 may be a rechargeable battery or a disposable battery. The internal battery 140 may be charged from an external power source device. The internal battery 140 may be charged by an external power source device through a communication link established through the communication interface 130.

The memory 150 may store the bio-signal data measured through the bio-signal measuring device 300. The bio-signal data is data generated by detecting a bio-signal of an object and refers to a signal having a frequency and an amplitude corresponding to a bio-signal measured in chronological order.

The memory 150 is hardware storing various types of data processed in the portable electronic device 100 and may store pieces of data processed by the processor 110 and pieces of data to be processed by the processor 110. The memory 150 may be implemented as various types, such as random access memory (RAM) such as dynamic random access memory (DRAM) and static random access memory (SRAM), read-only memory (ROM), and electrically erasable programmable read-only memory (EEPROM).

As shown in FIG. 3, the portable electronic device 100a may further include an external memory 160. The other components of the portable electronic device 100a are the same as those described with reference to FIG. 2, and thus, descriptions thereof will be omitted herein.

The external memory 160 is electrically connected to a processor 110 and stores data received through a Bluetooth module 120. The external memory 160 may be connected to the portable electronic device 100 through an additional connector and/or cable. The external memory 160 may further include a component for enabling charging using an additional cable even when the external memory 160 is connected to the portable electronic device 100.

Here, the processor 110 may encode bio-signal data with a preset encryption key and store the encoded bio-signal data in the external memory 160. Also, the processor 100 may store, in the external memory 160, an output control signal for outputting the bio-signal data and/or commands for processing of the output control signal. The processor 110 may transmit an encryption key or a decryption key for the bio-signal data before the output control signal.

The processor 110 may be designed to undergo a preset authentication process to access the external memory 160 and data stored in the external memory 160. For example, the processor 110 may receive the bio-signal data and/or the output control signal from the external memory 160 by inputting a preset password or undergoing a preset login process.

Figure 4:
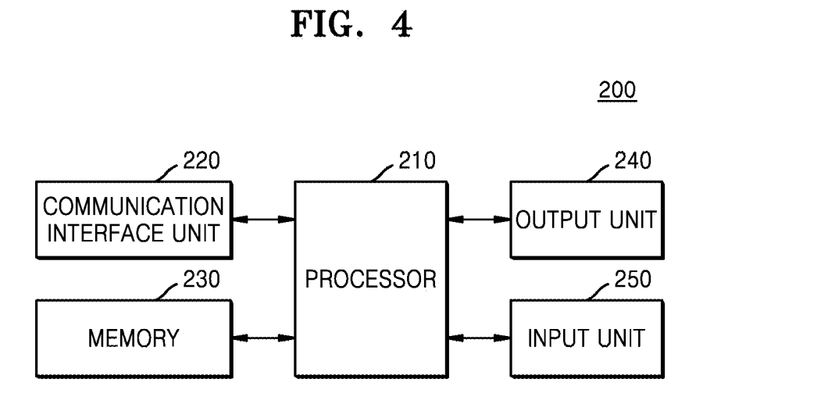
FIG. 4 is a block diagram of an electronic device according to one or more embodiments.

FIG. 4 is a block diagram of an electronic device 200 according to one or more embodiments.

As shown in FIG. 4, the electronic device 200 may include a processor 210, a communication interface unit 220, a memory 230, an output unit 240, and an input unit 250.

The processor 210 may be implemented to receive an output control signal of bio-signal data stored in the portable electronic device 100 recognized through the communication interface unit 220 and to output the bio-signal data received via the portable electronic device 100 through the output unit 240 according to the output control signal. The processor 210 may execute an authentication process under control of the portable electronic device 100. The authentication process may identify a password input through the portable electronic device 100 or the electronic device 200. The authentication process may identify a stored certificate in the electronic device 200. Also, the authentication process may be a login process to an external server.

Under control of the portable electronic device 100, a certificate stored in the memory 230 of the electronic device 200 may be considered to determine whether or not the portable electronic device 100 is approved. When the portable electronic device 100 is determined to be approved, the processor 210 may store the bio-signal data received via the portable electronic device 100 in the memory 230. When the portable electronic device 100 is determined to be approved, the processor 210 may transmit the bio-signal data to an external cloud server. When the portable electronic device 100 to which the electronic device 200 is connected is determined to be approved, the processor 210 may transmit the bio-signal data to a preset electronic address. The processor 210 may receive, in real time, bio-signal data measured through the bio-signal measuring device 300 and immediately output the bio-signal data through the output unit 240.

The communication interface unit 220 refers to an interface which communicates in a wired or wireless method. A USB is an example of the wired method of the communication interface unit 220, and WiFi is an example of the wireless method of the communication interface unit 220. The communication interface unit 220 may receive the bio-signal data from the portable electronic device 100.

The memory 230 may temporarily store data received from the portable electronic device 100. For example, the memory 230 may store the output control signal received from the portable electronic device 100 and delete the executed output control signal after the output is performed.

The memory 230 may permanently store data received from the portable electronic device 100. Data may be permanently stored in the memory 230 according to a control signal of the portable electronic device 100. The memory 230 may be implemented as various types, such as random access memory (RAM) such as dynamic random access memory (DRAM) and static random access memory (SRAM), read-only memory (ROM), hard disk driver, and electrically erasable programmable read-only memory (EEPROM or flash memory).

The output unit 240 may display a screen for providing information. A user interface generated by the processor 210 may be output. The output unit 240 may provide a screen for outputting the bio-signal data according to the control signal received from the portable electronic device 100. The output unit 240 may output the authentication process according to a control signal received from the portable electronic device 100. For example, the output unit 240 may include a display panel or the like for displaying a screen. Also, the output unit 240 may include a display panel, a speaker, or the like.

The input unit 250 may receive an input from a user. The input unit 250 may include an operation panel for receiving a user input. In detail, the input unit 250 may include devices capable of receiving various types of user inputs, such as a keyboard, a physical button, a touch screen, a camera, and a microphone. The input unit 250 may receive a preset user input under control of the portable electronic device 100. A user input that is input through the input unit 250 may be transmitted to the portable electronic device 100 through the communication interface unit 220.

The electronic device 200 communicates with the portable electronic device 100 and outputs data received from the bio-signal measuring device 300 or performs an operation under control of the portable electronic device 100.

FIGS. 5 through 8 are flowcharts according to one or more embodiments.

Figure 5:
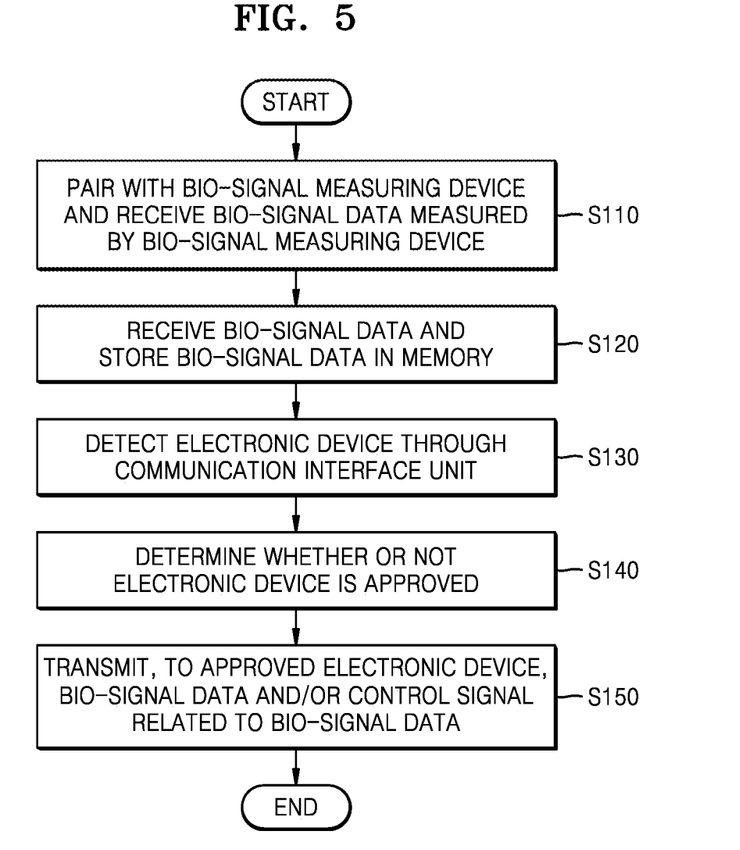
FIG. 5 is a flowchart showing a method of operation of a portable electronic device according to one or more embodiments.

FIG. 5 is a flowchart of a method of operation of the portable electronic device 100. In operation S110, the portable electronic device 100 is paired with the bio-signal measuring device 300 and receives bio-signal data measured by the bio-signal measuring device 300.

In operation S120, the portable electronic device 100 stores the received bio-signal data in a memory.

In operation S130, the portable electronic device 100 may detect or recognize the electronic device 200 through a communication interface unit. The portable electronic device 100 may detect connection of the electronic device 200 through the communication interface unit on the basis of periodical connection detection or an interrupt signal.

In operation S140, the portable electronic device 100 determines whether or not the electronic device 200 is approved by receiving preset authentication data from the detected electronic device 200. The authentication data may be generated on the basis of data stored in the electronic device 200, code input by a user, or identification information stored in a system area of the electronic device 200. The portable electronic device 100 may determine whether or not the electronic device 200 is approved by receiving, from the electronic device 200, various types of authentication data such as a password, an ID and a password, or a stored certificate.

In operation S150, the portable electronic device 100 transmits, to the electronic device 200 that was approved, the bio-signal data and/or a control signal related to the bio-signal data. Through the electronic device 200, which is preregistered or approved, the portable electronic device 100 may output a bio-signal, store the bio-signal, or transmit the bio-signal to another device.

Figure 6:
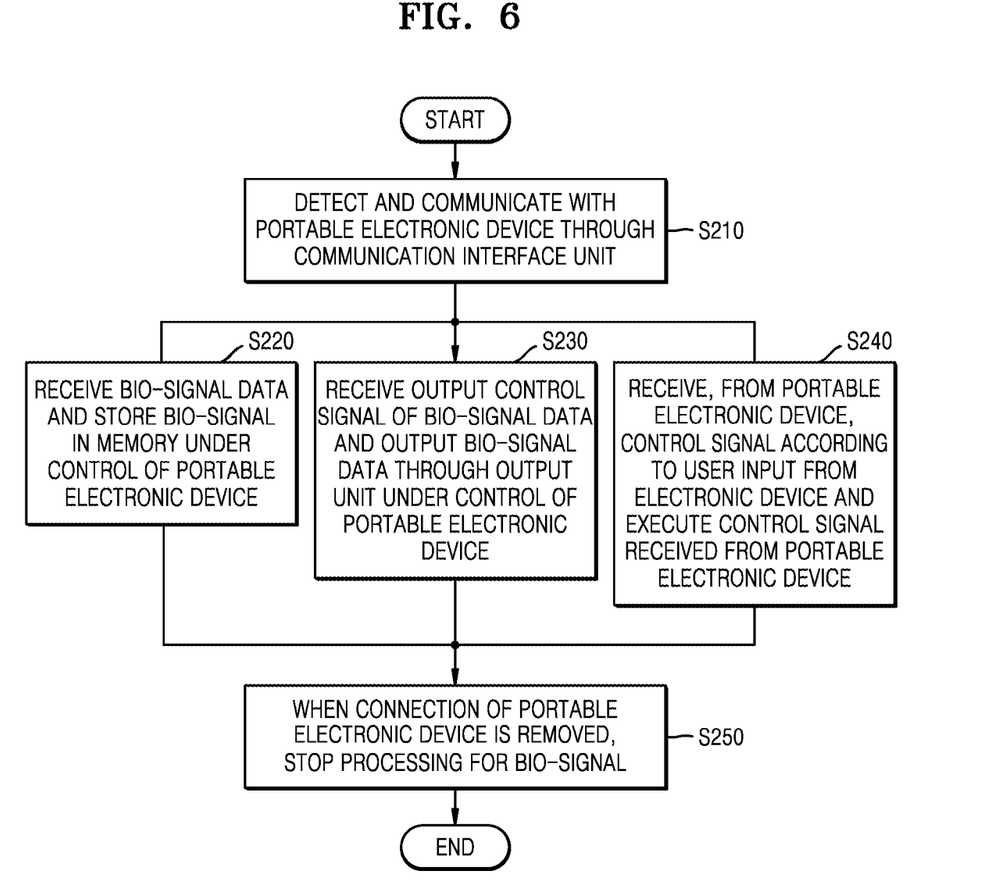
FIG. 6 is a flowchart showing a method of operation of another portable electronic device according to one or more embodiments.

FIG. 6 is a flowchart of a method of operation of the electronic device 200, which receives bio-signal data from the portable electronic device 100.

In operation S210, the electronic device 200, which receives the bio-signal data, detects and communicates with the portable electronic device 100 through a communication interface unit.

In operation S220, the electronic device 200, which receives the bio-signal data, may receive the bio-signal data and store the bio-signal data in a memory under control of the portable electronic device 100. The electronic device 200 may output a preset user interface to control the portable electronic device 100.

In operation S230, the electronic device 200, which receives the bio-signal data, may receive an output control signal of the bio-signal data and output the bio-signal data through an output unit under control of the portable electronic device 100.

In operation S240, the electronic device 200, which receives the bio-signal data, may transmit, to the portable electronic device 100, a user input that is input by a request of the portable electronic device 100 and execute a control signal received from the portable electronic device 100.

In operation S250, the electronic device 200, which receives the bio-signal data, may stop processing for a bio-signal when connection of the portable electronic device 100 is removed.

Figure 7:
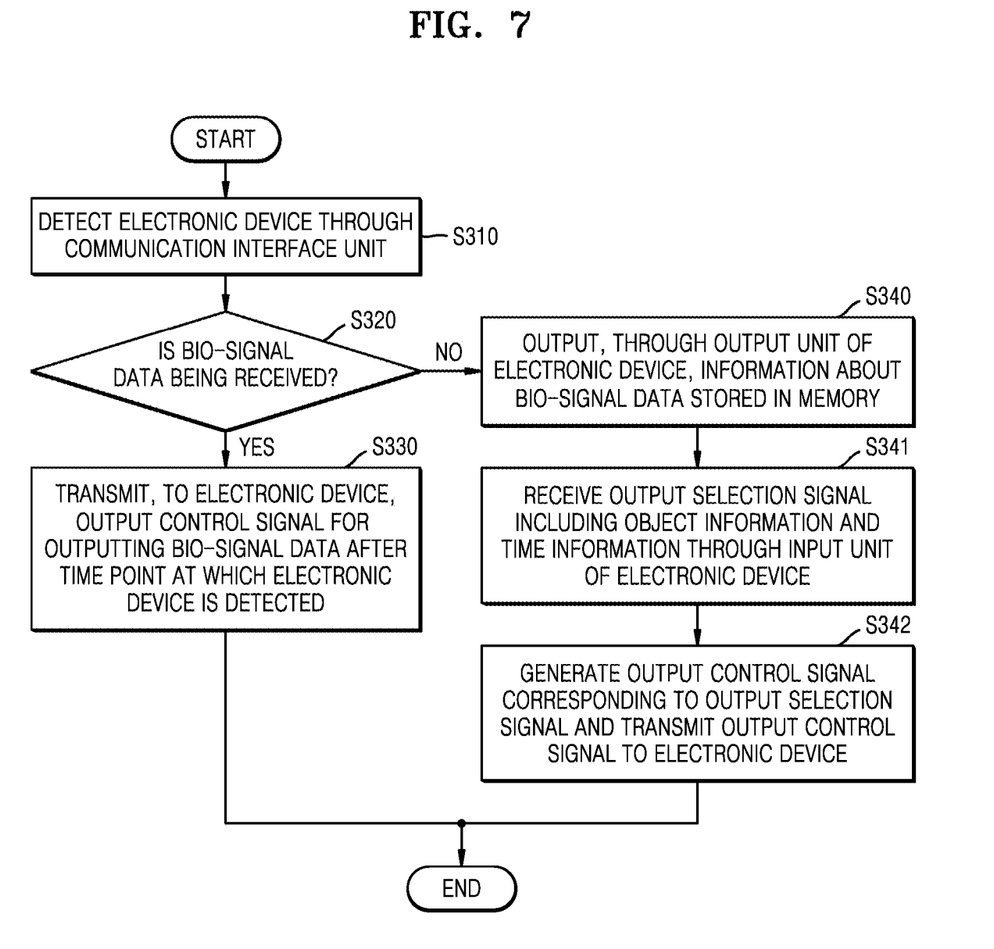
FIG. 7 is a flowchart showing operations between two portable electronic devices according to one or more embodiments.
Figure 8:
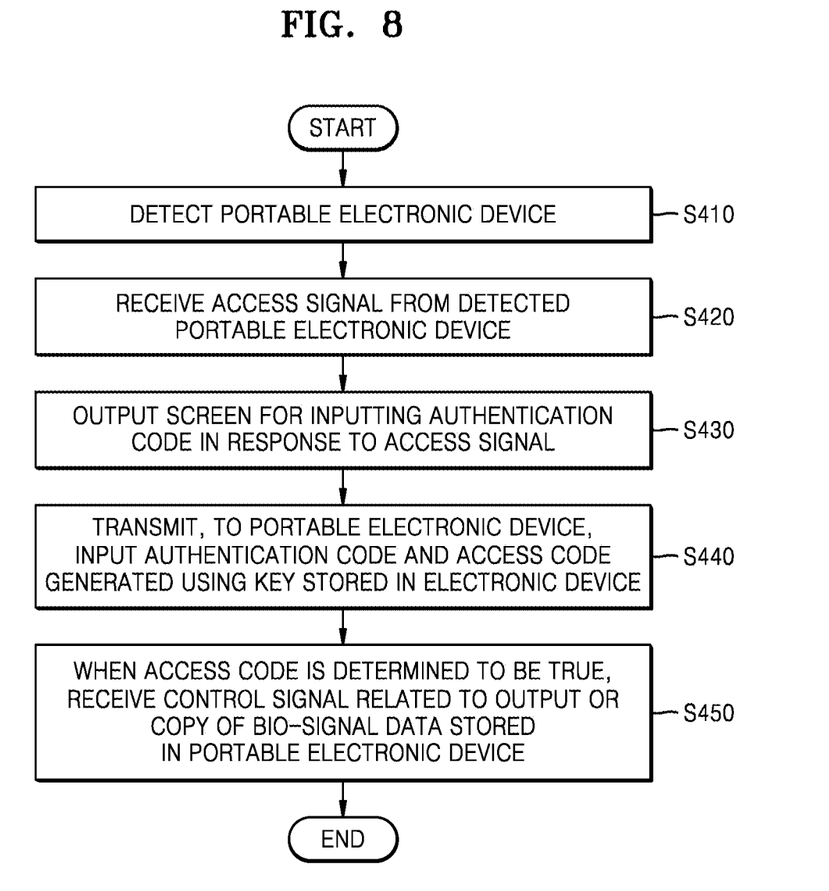
FIG. 8 is a flowchart showing other operations between two portable electronic devices according to one or more embodiments.

FIG. 7 is a flowchart showing operations between two portable electronic devices 100, 200 according to one or more embodiments. FIG. 8 is a flowchart showing other operations between two portable electronic devices 200, 100 according to one or more embodiments;

As shown in FIG. 7, in operation S310, the portable electronic device 100 may detect the electronic device 200 through a communication interface unit. The portable electronic device 100 may establish a communication session for communicating with the detected electronic device 200.

In operation S320, the portable electronic device 100 may determine whether or not the portable electronic device 100 is in a state of receiving bio-signal data while being connected to the electronic device 200. The portable electronic device 100 may determine whether or not the portable electronic device 100 is in the state of receiving the bio-signal data on the basis of whether or not the portable electronic device 100 is communicating with the bio-signal measuring device 300 and is in a state of receiving data from the bio-signal measuring device 300.

In operation S330, after a time point at which the electronic device 200 is detected, the portable electronic device 100 may transmit, to the electronic device 200, an output control signal implemented to output the bio-signal data received from the bio-signal measuring device 300 while being connected to the electronic device 200. In this case, the output control signal may be a signal that controls data received from the bio-signal measuring device 300 to be output in real time or after a preset time (after a very short time).

In operation S340, the portable electronic device 100 may output information about the bio-signal data stored in a memory through an output unit of the electronic device 200.

In operation S341, the portable electronic device 100 may receive, through an input unit of the electronic device 200, an output selection signal including object information and time information. The portable electronic device 100 may provide a screen for selecting the object information and the time information to be output in response to an access signal from the electronic device 200. The object information may be information about an object from which bio-signal data is to be measured and may be information about a living body such as a person or an animal. The object information refers to information about an object to be output. The time information may include a start value, an end value, and the like of a particular time at which the bio-signal data is to be output, from among a time interval in which the bio-signal data is recorded.

In operation S342, the portable electronic device 100 may generate the output control signal corresponding to the output selection signal and transmit the output control signal to the electronic device 200. The portable electronic device 100 may specify the object information and the time information included in the output selection signal and extract bio-signal data based on the object information and the time information. The portable electronic device 100 may generate an output control signal including commands output by a user interface outputting the bio-signal data and transmit the output control signal to the electronic device 200. The output control signal may be generated considering the resolution of the electronic device 200.

The electronic device 200 may output an output screen in response to the received output control signal. As a result, measured bio-signal data may be outputted through the electronic device 200.

As shown in FIG. 8, in operation S410, the electronic device 200 may detect the portable electronic device 100.

In operation S420, the electronic device 200 may receive an access signal from the detected portable electronic device 100.

In operation S430, the electronic device 200 may output a screen for inputting an authentication code in response to the access signal.

In operation S440, the electronic device 200 may transmit, to the portable electronic device 100, the input authentication code or an access code generated using a key stored in the electronic device 200. The key stored in the electronic device 200 may include at least one of an identification code, a phone number, and a serial code of the electronic device 200. The authentication code may be acquired through the portable electronic device 100 or another electronic device 200.

In operation S450, when the access code is determined to be true, the electronic device 200 may receive a control signal related to an output or copy of the bio-signal data stored in the portable electronic device 100. The access code may be determined to be true through the portable electronic device 100.

Figure 9:
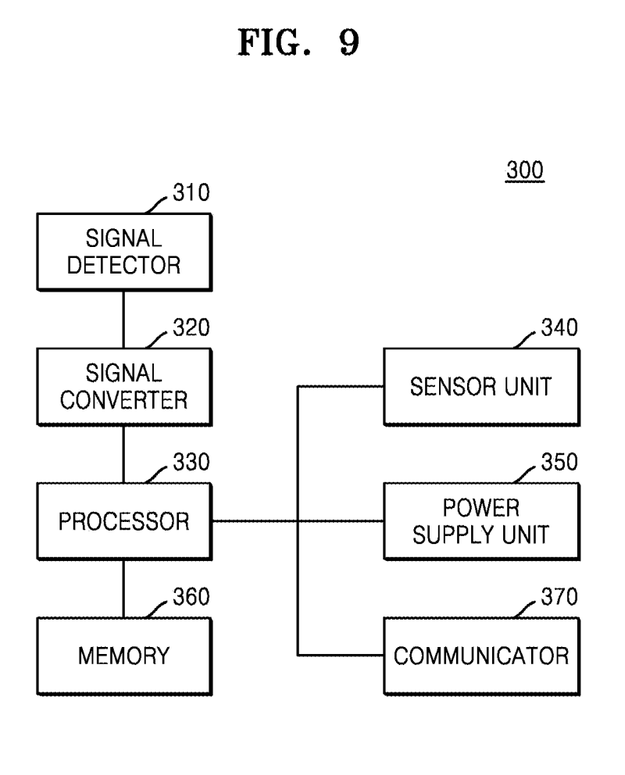
FIG. 9 is a block diagram of a bio-signal measuring device according to one or more embodiments.

FIG. 9 is a block diagram of an electrocardiogram measuring device 300 according to one or more embodiments.

As shown in FIG. 9, the electrocardiogram measuring device 300 may include a signal detector 310, a signal converter 320, a processor 330, a sensor unit 340, a power supply unit 350, a memory 360, and a communicator 370 to detect an electrical signal generated from the heart of an object.

The signal detector 310 may detect a bio-signal such as blood pressure, blood sugar, heartrate, oxygen saturation level, sleep time, depression diagnosis, chemical analysis, weight, the amount of exercise, or an electrocardiogram. The signal detector 310 outputs an electrocardiogram analog signal by detecting an electrical signal from the heart of an object. The signal converter 320 may convert the bio-signal into a digital signal. The signal converter 320 may convert the electrocardiogram analog signal into an electrocardiogram digital signal.

The processor 330 may be implemented to operate in several operation modes in association with processing of the electrocardiogram digital signal. The processor 330 may operate in one of a first operation mode for storing the electrocardiogram digital signal in the memory 360 and a second operation mode for transmitting the electrocardiogram digital signal to an external electronic device. The processor 330 may operate in the first operation mode or the second operation mode or may operate simultaneously in the first operation mode and the second operation mode.

In the second operation mode, the processor 330 may transmit, to the external electronic device, the electrocardiogram digital signal stored in the memory 360. The external electronic device may be implemented as a smartphone, a table personal computer (PC), a mobile phone, a video phone, an e-book reader, a desktop PC, a laptop PC, a netbook computer, a workstation, a server, a personal digital assistant (PDA), a portable multimedia player (PMP), an MP3 player, a mobile medical device, a camera, a wearable device, or the like, including one or more processors. The external electronic device includes a memory and may be in the form of a storage medium including a processor for controlling the memory. The external electronic device may include a communication interface for communicating with the electrocardiogram measuring device 300 or may be connected to an additional communication interface to operate.

In the first operation mode, the processor 330 may store, in the memory, an electrocardiogram digital signal merged with a user input. The processor 330 may receive the user input from an input unit (not shown), which is electrically connected, or a user terminal, which is connected through a communication network. The processor 330 may convert an electrocardiogram signal by using the received user input and generation time information of the user input.

In the first operation mode, the processor 330 may merge the electrocardiogram digital signal with the user input and store, in the memory 360, the electrocardiogram digital signal merged with the user input by using the generation time information of the user input.

In the second operation mode, the processor 330 may transmit, to the external electronic device, the electrocardiogram digital signal merged with the user input. The external electronic device may store the received electrocardiogram digital signal in a memory or may output the received electrocardiogram digital signal through an output unit.

The processor 330 may automatically change an operation mode considering a communication state with the external electronic device. For example, when the communication state with the external electronic device is abnormal, the processor 330 may stop the second operation mode and change the second operation mode to the first operation mode to operate.

When the communication state is normal again, the operation mode is changed to the second operation mode again. After the operation mode is changed to the second operation mode, an electrocardiogram digital signal measured in real time may be transmitted to the external electronic device.

The processor 330 may further include a temperature sensor, a motion sensor, a proximity sensor, a sound sensor, or the like.

The processor 330 may generate an electrocardiogram digital signal merged with a tag corresponding to information acquired by analyzing the electrocardiogram digital signal. The processor 330 may operate in the first operation mode and/or the second operation mode for the electrocardiogram digital signal merged with the tag.

The information acquired by analyzing the electrocardiogram digital signal may be a heartrate, cardiac component information, the maximum magnitude value, time information of a cardiac feature point, waveform magnitude information of the cardiac feature point, or the like. The maximum magnitude value refers to the maximum value of the magnitude from among the signal magnitudes of the electrocardiogram digital signal. The cardiac feature point refers to a point at which a slope of a differential value of the electrocardiogram digital signal changes from positive to negative or negative to positive. The processor 330 may store, in the memory 360, a tag including at least one of the heartrate, the maximum magnitude value, the time information of the cardiac feature point, and the waveform magnitude information of the cardiac feature point acquired by analyzing the electrocardiogram digital signal, in association with the electrocardiogram digital signal.

The processor 330 may acquire the amount of exercise of an object, further generate a tag corresponding to the exercise amount, and merge the tag corresponding to the exercise amount with the electrocardiogram digital signal.

In the second operation mode, the processor 330 may transmit in real time, to the external electronic device, the electrocardiogram digital signal merged with the user input or the tag. Alternatively, when the measurement of the electrocardiogram digital signal is completed, the processor 330 may transmit, to the external electronic device 100, 200, the electrocardiogram digital signal stored in the memory 360. When the measurement of the electrocardiogram digital signal is completed, the processor 330 may generate a measurement completion signal and start uploading, to the external electronic device, the electrocardiogram digital signal stored in the memory 360 by the measurement completion signal. The measurement completion signal may be generated by an input from the external electronic device, an input from an input unit (not shown), or a preset measurement time, or may be generated after a preset measurement time from a measurement start time.

The power supply unit 350 supplies power to the signal detector 310, the signal converter 320, the processor 330, the sensor unit 340, the memory 360, the communicator 370, and the like. The power supply unit 350 may use a rechargeable battery or a disposable battery.

The memory 360 may store data related to measurement of an electrocardiogram. The memory 360 may store information about the object, a measurement time, and data related to a measured electrocardiogram. The memory 360 may be hardware storing various types of data processed in the electrocardiogram measuring device 300 and may store pieces of data processed by the processor 330 and pieces of data to be processed by the processor 330. The memory 360 may store a generated input and a tag related to the input. The memory 360 may store an electrocardiogram digital signal and an electrocardiogram digital signal synchronized with a tag. The memory 360 may be implemented as various types, such as random access memory (RAM) such as dynamic random access memory (DRAM) and static random access memory (SRAM), read-only memory (ROM), and electrically erasable programmable read-only memory (EEPROM or flash memory).

The sensor unit 340 senses temperature or movement. The sensor unit 340 may sense movements in x, y, and z-axis directions, angular movement, and roll-pitch-yaw rotational movement. The sensor unit 340 may sense the momentum of a device, a temperature value of the device, physical pressure applied to the device, and the like. The sensor unit 340 may include an element for sensing temperature, an element for sensing motion, an element of sensing pressure, and the like.

The communicator 370 may receive a control signal from an external user terminal. The communicator 370 may transmit measured data to the external user terminal.

The device described above may be implemented with hardware components, software components, and/or combinations of hardware components and software components. For example, the apparatus and components described in one or more embodiments may be implemented, for example, by using one or more general-purpose computers or special-purpose computers such as a processor, a controller, an arithmetic logic unit (ALU), a digital signal processor, a microcomputer, a field programmable gate array (FPGA), a programmable logic unit (PLU), a microprocessor, or any other devices capable of executing and responding to instructions. A processing unit may perform an operating system (OS) and one or more software applications executed on the OS. Also, the processing unit may access, store, control, process, and generate data in response to execution of software. For convenience of understanding, while one processing unit has been described as being used, it will be understood by one of ordinary skill in the art that the processing unit may include a plurality of processing elements and/or a plurality of types of processing elements. For example, the processing unit may include a plurality of processors or one processor and one controller. Also, the processing unit may include another processing configuration such as a parallel processor.

Software may include a computer program, code, instructions, or a combination of one or more thereof and may configure the processing unit to operate as wanted or instruct the processing unit independently or collectively. Software and/or data may be permanently or temporarily embodied in any type of machine, component, physical device, virtual equipment, computer storage medium or device, or transmitted signal wave to be interpreted by the processing unit or to provide the processing unit with instructions or data. Software may be distributed over networked computer systems and may be stored or executed in a distributed manner. Software and/or data may be stored on one or more computer-readable recording media.

The method according to one or more embodiments may be implemented in the form of a computer instruction that may be executed through various types of computer units and recorded on a computer-readable recording medium. The computer-readable recording medium may include program instructions, data files, data structures, or the like alone or in combination. The program instructions recorded on the medium may be specially designed and configured for an embodiment or may be known and available to one of ordinary skill in computer software. Examples of the computer-readable recording medium include magnetic media such as hard disks, floppy disks, and magnetic tapes, optical media such as a CD-ROM and a DVD, magneto-optical media such as floptical disks, and hardware devices specially configured to store and perform program instructions such as ROM, RAM, and flash memory. Examples of the program instructions include high-level language code that may be executed by a computer using an interpreter or the like, as well as machine language code made by a compiler. The hardware device described above may be configured to operate as one or more software modules to perform operations of the embodiments, and the reverse is the same.

According to one embodiment as described above, a portable electronic device may receive bio-signal data from a measuring device, and store and carry the bio-signal data.

Also, bio-signal data stored in the portable electronic device or bio-signal data received through the portable electronic device may be provided through an output unit of an electronic device connected to the portable electronic device.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. An electrocardiogram measuring system comprising:
an electrocardiogram measuring device comprising:
a signal detector detecting an electrocardiogram analog signal;
a signal converter converting the electrocardiogram analog signal into an electrocardiogram digital signal;
a memory;
a communicator communicating with an external device; and
a processor configured to cause the electrocardiogram measuring device to operate in a first operation mode for storing the electrocardiogram digital signal in the memory and a second operation mode for transmitting the electrocardiogram digital signal to the external device; and
a portable electronic device communicatively coupled to the electrocardiogram measuring device and the external device, the portable electronic device configured to facilitate the second operation mode of transmitting the electrocardiogram digital signal from the electrocardiogram measuring device to the external device by pre-storing an identification (ID) of the external device, accessing a certificate stored in the external device, and authenticating the certificate of the external device,
the portable electronic device further configured to transmit the electrocardiogram digital signal to the external device to store the electrocardiogram digital signal in the external device.

2. The electrocardiogram measuring system of claim 1, wherein the processor is configured to transmit the electrocardiogram digital signal to a cloud server.

3. The electrocardiogram measuring system of claim 1, wherein the portable electronic device is configured to select the external device by a program.

4. The electrocardiogram measuring system of claim 3, wherein the program is stored in the portable electronic device.

5. The electrocardiogram measuring system of claim 1, wherein the electrocardiogram digital signal is transmitted to the portable electronic device and generated on an output display of the portable electronic device before the portable electronic device connect to the external device.

6. The electrocardiogram measuring system of claim 1, wherein the electrocardiogram digital signal is transmitted to the external device and generated on an output display of the external device while connected to the electrocardiogram measuring device.

7. The electrocardiogram measuring system of claim 1, wherein the portable electronic device is configured to run authenticating the certificate of the external device by user input while the electrocardiogram digital signal is output on an output unit of the portable electronic device.

8. The electrocardiogram measuring system of claim 1, wherein the portable electronic device is configured to transmit the electrocardiogram digital signal to one or more device.

9. The electrocardiogram measuring system of claim 1, wherein the portable electronic device further comprises an external memory, and the external memory stores the electrocardiogram digital signal.

10. An electrocardiogram measuring method comprising:
communicating, by a portable electronic device including a processor, with an electrocardiogram measuring device and an external device,
wherein the electrocardiogram measuring device is communicatively coupled to the external device and configured to detect an electrocardiogram analog signal, convert the electrocardiogram analog signal into an electrocardiogram digital signal, and set an operation mode to a first operation mode for storing the electrocardiogram digital signal in a memory or a second operation mode for transmitting the electrocardiogram digital signal to an external device;
facilitating, by the portable electronic device, the second operation mode of transmitting the electrocardiogram digital signal from the electrocardiogram measuring device to the external device by pre-storing an identification (ID) of the external device, accessing a certificate stored in the external device, and authenticating the external device; and
transmitting, by the portable electronic device, the electrocardiogram digital signal to the external device so that the electrocardiogram digital signal is stored in the external device.

11. The electrocardiogram measuring method of claim 10, further comprising:
while the portable electronic device is running, displaying the electrocardiogram digital signal by the portable electronic device.

12. The electrocardiogram measuring method of claim 10, further comprising: storing, by the portable electronic device, the electrocardiogram digital signal in the memory or a cloud server through a network.

13. The electrocardiogram measuring method of claim 11, further comprising:
controlling, by the portable electronic device, a user interface for outputting the electrocardiogram digital signal and object information to be displayed at the external device while connected to the electrocardiogram measuring device.

14. The electrocardiogram measuring method of claim 10, further comprising controlling, by the portable electronic device, the electrocardiogram digital signal to be displayed at the external device while connected to the electrocardiogram measuring device.

* * * * *